US011257190B2

(12) United States Patent
Mao et al.

(10) Patent No.: US 11,257,190 B2
(45) Date of Patent: Feb. 22, 2022

(54) IMAGE QUALITY IMPROVEMENT METHODS FOR OPTICAL COHERENCE TOMOGRAPHY

(71) Applicant: Topcon Corporation, Tokyo (JP)

(72) Inventors: Zaixing Mao, Edgewater, NJ (US); Zhenguo Wang, Ridgewood, NJ (US); Kinpui Chan, Ridgewood, NJ (US)

(73) Assignee: TOPCON CORPORATION, Tokyo (JP)

(*) Notice: Subject to any disclaimer, the term of this patent is extended or adjusted under 35 U.S.C. 154(b) by 62 days.

(21) Appl. No.: 16/797,848

(22) Filed: Feb. 21, 2020

(65) Prior Publication Data

US 2020/0279352 A1    Sep. 3, 2020

Related U.S. Application Data

(60) Provisional application No. 62/812,728, filed on Mar. 1, 2019.

(51) Int. Cl.
*G06T 5/00* (2006.01)
*G06T 5/50* (2006.01)

(52) U.S. Cl.
CPC .............. *G06T 5/002* (2013.01); *G06T 5/004* (2013.01); *G06T 5/50* (2013.01); *G06T 2207/10101* (2013.01); *G06T 2207/20081* (2013.01); *G06T 2207/20216* (2013.01); *G06T 2207/30041* (2013.01)

(58) Field of Classification Search
CPC ........... G06T 5/002; G06T 5/004; G06T 5/20; G06T 5/50; G06T 2207/10101; G06T 2207/20081; G06T 2207/20216; G06T 2207/30041; G06T 2207/20076; A61B 5/0066; A61B 5/7203
See application file for complete search history.

(56) References Cited

U.S. PATENT DOCUMENTS 9,704,224 B2 *  7/2017  Lee ...................... A61B 6/5258
9,984,459 B2 *  5/2018  Reisman ................... G06T 5/50
(Continued)

FOREIGN PATENT DOCUMENTS

CN      105359185 A  *  2/2016  .......... A61B 6/5258
EP        2099224 A1     9/2009
(Continued)

OTHER PUBLICATIONS

Extended European Search Report for European Application No. 20159835.6 dated Sep. 10, 2020.
(Continued)

*Primary Examiner* — Matthew C Bella
*Assistant Examiner* — Kathleen M Broughton
(74) *Attorney, Agent, or Firm* — Pearne & Gordon LLP

(57) ABSTRACT

Ophthalmological images generated by coherent imaging modalities have multiple types of noise, including random noise caused by the imaging system and speckle noise caused by turbid objects such as living tissues. These noises can occur at different levels in different locations. A noise-reduction method and system of the present disclosure thus relates to applying different filters for different types of noise and/or different locations of images, sequentially or in parallel and combined, to produce a final noise-reduced image.

13 Claims, 15 Drawing Sheets

(56) References Cited

U.S. PATENT DOCUMENTS

| | | | |
|---|---|---|---|
| 2005/0157796 A1 | 7/2005 | Suzuki | |
| 2006/0245506 A1 | 11/2006 | Lin et al. | |
| 2008/0247620 A1* | 10/2008 | Lewis | G06T 19/006 382/128 |
| 2013/0243318 A1* | 9/2013 | Honda | H04N 9/0451 382/167 |
| 2017/0319059 A1* | 11/2017 | Cheng | G06T 5/002 |
| 2018/0137605 A1* | 5/2018 | Otsuka | G06T 5/50 |

FOREIGN PATENT DOCUMENTS

| | | | |
|---|---|---|---|
| JP | 2013201724 A | * 10/2013 | |
| WO | WO-2018159689 A1 | * 9/2018 | C04B 35/64 |

OTHER PUBLICATIONS

Agostinelli, et al., "Adaptive Multi-Column Deep Neural Networks with Application to Robust Image Denoising", IEEE Transactions on Neural Networks and Learning Systems, Jan. 1, 2013, XP055568209, ISSN: 2162-237X, vol. 29, pp. 1493-1501.

Devalla, et al., "A Deep Learning Approach to Denoise Optical Coherence Tomography Images of the Optic Nerve Head", Scientific Reports, www.nature.com/scientifcreports; Oct. 8, 2019, pp. 1-13.

Halupka, et al., "Retinal optical coherence tomography image enhancement via deep learning", Biomedical Optics Express, vol. 9, No. 12, Dec. 1, 2018, pp. 6205-6221.

Li, et al., "Statistical model for OCT image denoising", Biomedical Optics Express, vol. 8, No. 9, Sep. 1, 2017, pp. 3903-3917.

Ma, et al., "Speckle noise reduction in optical coherence tomography images based on edge-sensitive cGAN", Biomedical Optics Express, vol. 9, No. 11, Nov. 1, 2018, pp. 5129-5146.

Esmaeili, et al., "Speckle Noise in Optical Coherence Tomography Using Two-dimensional Curvelet-based Dictionary Learning", Journal of Medical Signals and Sensors, vol. 7, No. 2, Apr.-Jun. 2017, pp. 86-91.

Liu et al., "Connecting Image Denoising and High-Level Vision Tasks via Deep Learning", IEEE Transations on Image Processing, Sep. 6, 2018, pp. 3695-3706, XP55698602.

Partial European Search Report for European Application No. 20159835.6 dated May 26, 2020.

* cited by examiner

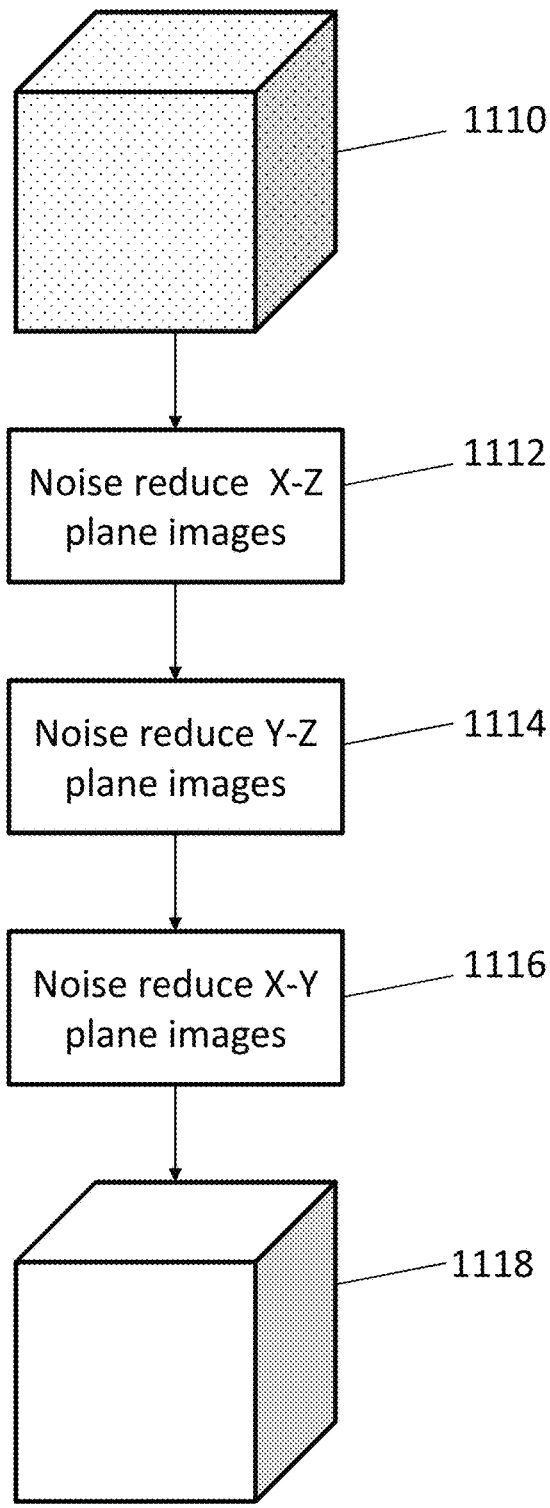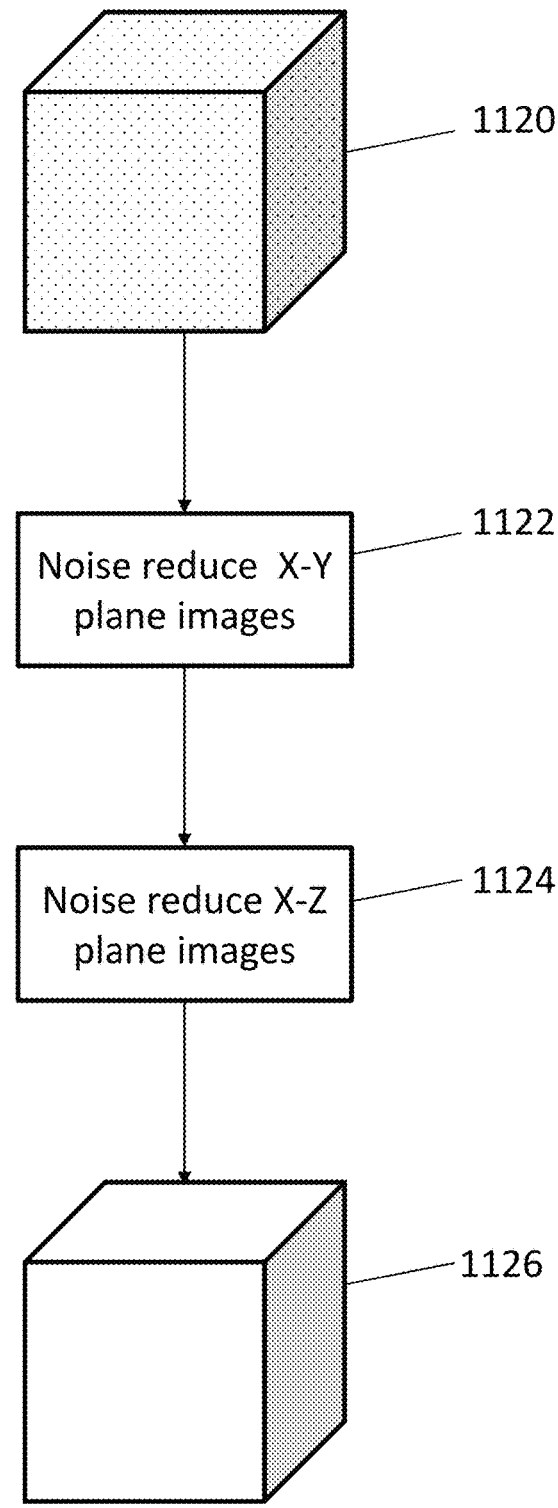
Figure 11B
Figure 11C

IMAGE QUALITY IMPROVEMENT METHODS FOR OPTICAL COHERENCE TOMOGRAPHY

CROSS-REFERENCE TO RELATED APPLICATIONS

This application claims priority to U.S. Provisional Application Ser. No. 62/812,728, filed on Mar. 1, 2019, entitled "IMAGE QUALITY IMPROVEMENT METHODS FOR OPTICAL COHERENCE TOMOGRAPHY," the entirety of which is incorporated herein by reference.

BACKGROUND OF THE INVENTION

Coherent imaging modalities (e.g., optical coherence tomography (OCT)) are subject to noise, which can degrade final image quality. In particular with ophthalmological imaging, the presence of noise can significantly degrade imaging fidelity and can lead to errors during segmentation of retinal layers (e.g., during segmentation of B-scans or like images including a depth dimension). These segmentation errors can further lead to errors in analysis of the images based on the segmentation, and thus ultimately, errors in diagnosis and treatment of an imaged subject.

Currently, noise is treated by applying a common filter to an underlying set of data or images produced from that data. However, these filters are unable to remove all noise at appropriate levels. Further, noise reduction systems, and methods that utilize a large number of sample data and images to normalize noise are still subject to noises and errors that persist throughout the sample sets. Therefore, the images can still lack quality, and segmentation and analysis can still be prone to errors.

BRIEF SUMMARY OF THE INVENTION

According to a first example, an image processing method comprises: applying a first filter to an input image, thereby generating a first noise-reduced image; applying a second filter to the input image, thereby generating a second noise-reduced image; and combining the first noise-reduced image and the second noise-reduced image, thereby generating a final noise-reduced image, wherein the first filter is configured to suppress a first type of noise from the input image and the second filter is configured to suppress a second type of noise from the input image, the first and second types of noise being different.

In various embodiments of the first example, the first noise-reduced image and the second noise-reduced images are combined by weighted averaging, the first noise-reduced image being weighted according to a level of the first type of noise in the input image and the second noise-reduced image being weighted according to a level of the second type of noise in the input image; the first noise-reduced image and the second noise-reduced images are combined, or the first and/or second noise-reduced images are produced, by a machine learning system; an intensity of at least one pixel of the first noise-reduced image is set by the first filter to correspond to a maximum intensity of a probability distribution of intensities of pixels at a corresponding location of an object in the image; the probability distribution is determined by a machine learning system; the first type of noise is random noise or noise caused by an imaging system that captured the input image; the first filter is a machine learning system trained with images taken from the same or substantially the same location as the input image; the first type of noise is speckle noise; the first filter is a machine learning system trained with images taken from locations adjacent to or nearby a location of the input image; the input image is an optical coherence tomography (OCT) or OCT-angiography B-scan image; the input image is an en face optical coherence tomography (OCT) or OCT-angiography image; the input image is obtained by an optical coherence tomography imaging system configured to operate at least at a 400 kHz A-line rate; the input image is an image of a retina; the method further comprises segmenting the input image as a result of applying the first filter and the second filter; and/or the method further comprises displaying the final noise-reduced image in real-time with the capturing of the input image.

According to a second example, an image processing method comprises: filtering a first input image; filtering a second input image; and combining the filtered first input image and the filtered second input image, thereby generating a final noise-reduced volume, wherein the first input image and the second input image are different 2D images of a 3D volume, and wherein the first input image and the second input image are from different planes and/or en face images of different reference layers of the 3D volume.

In various embodiments of the second example, filtering the first input image comprises: applying a first filter to the first input image, thereby generating a first noise-reduced image; applying a second filter to the first input image, thereby generating a second noise-reduced image; and combining the first noise-reduced image and the second noise-reduced image, thereby generating a final noise-reduced image, wherein the first filter is configured to suppress a first type of noise from the first input image and the second filter is configured to suppress a second type of noise from the first input image, the first and second types of noise being different.

BRIEF DESCRIPTION OF THE SEVERAL VIEWS OF THE DRAWING

FIGS. 11A, 11B, 11C, and 11D illustrate example volumetric noise reduction methods according to the present disclosure.

DETAILED DESCRIPTION OF THE INVENTION

In view of the above, the present disclosure is directed to improvements in noise reduction for coherent imaging modalities. It is now recognized that more than one type of noise exists in images from coherent imaging modalities, and the types and levels of the noise can vary between pixels of an image. These types of noise include: 1) random noise from the system; and 2) speckle variation (noise) caused by the coherent imaging modalities or objects being imaged (e.g., a subject's eye or other biological tissue). The speckle noise may arise from interference of light waves having random phases, for example, as light scattered from various points of turbid object being imaged. As suggested above, while existing noise reductions methods and systems exist they are directed to treating the different types of noise with the same filter. And other machine learning based methods improperly rely on a substantial number of averaged images that can induce errors in the filtering process.

Figure 1:
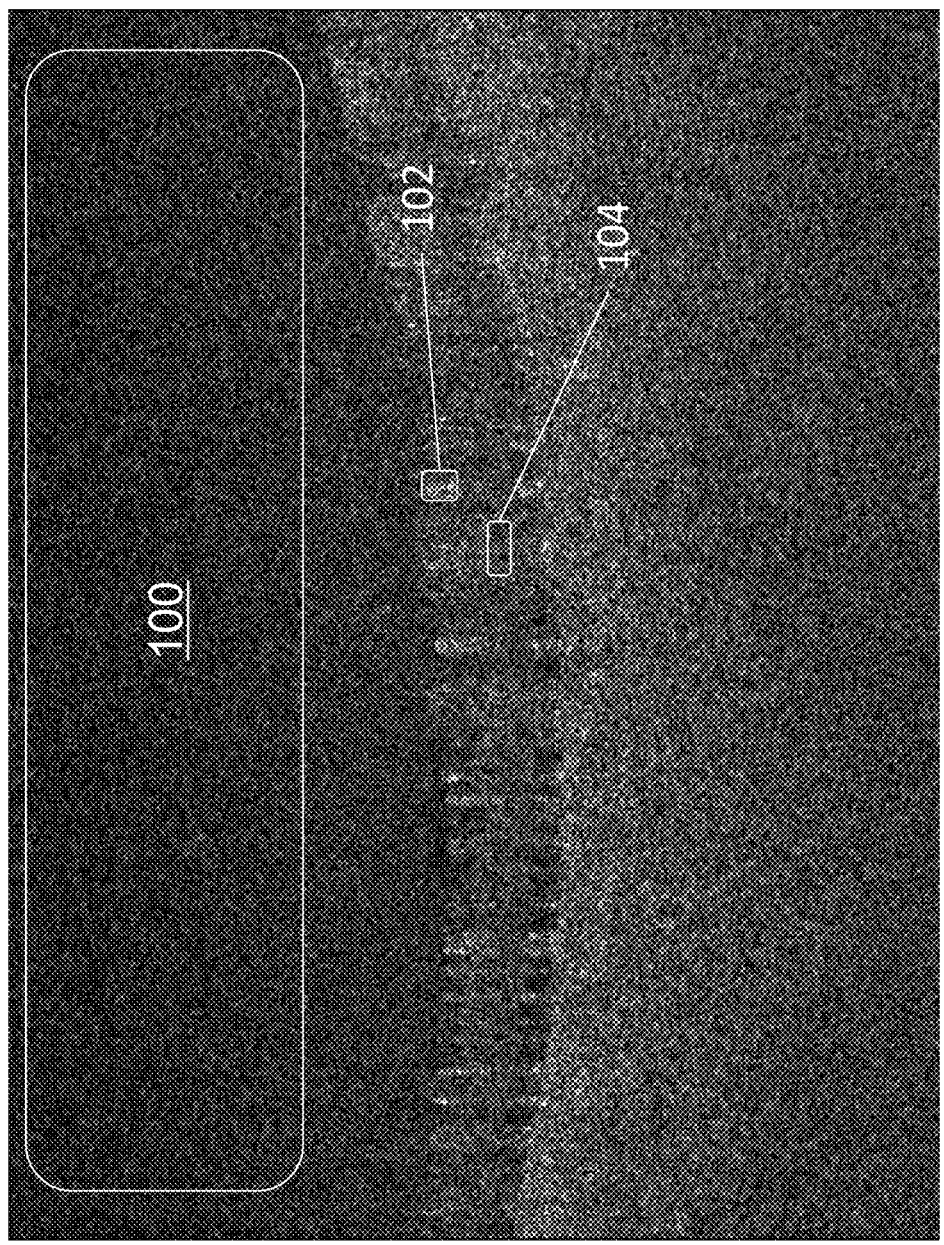
FIG. 1 illustrates noise as an image of the absolute difference between each pixel of two OCT B-scan images generated from scans of essentially the same location of a subject's eye at different times.

The aforementioned two types of noise can be seen with respect to FIG. 1, which illustrates an image showing the absolute difference between each pixel of two OCT B-scan images generated from scans of essentially the same location of a subject's eye at different times. It is noted that the reference to OCT images is merely an example and that the systems and methods described by the present application are applicable to images generated by any coherent imaging technique. Because the general structure at the location is unchanged, the difference between the two images represents noise, where the brightness of each pixel corresponds to the level of noise.

Three regions of noise are identified in FIG. 1. The first region 100 is an area above the retina, which includes random noise from the imaging system. The second region 102 in the retinal tissue includes speckle variation due to blood flow as well as the random noise in the system. The third region 104 in the retinal tissue similarly includes other speckle variation due to live biological tissues (such as blood flow) as well as the random noise in the system.

Figure 2A:
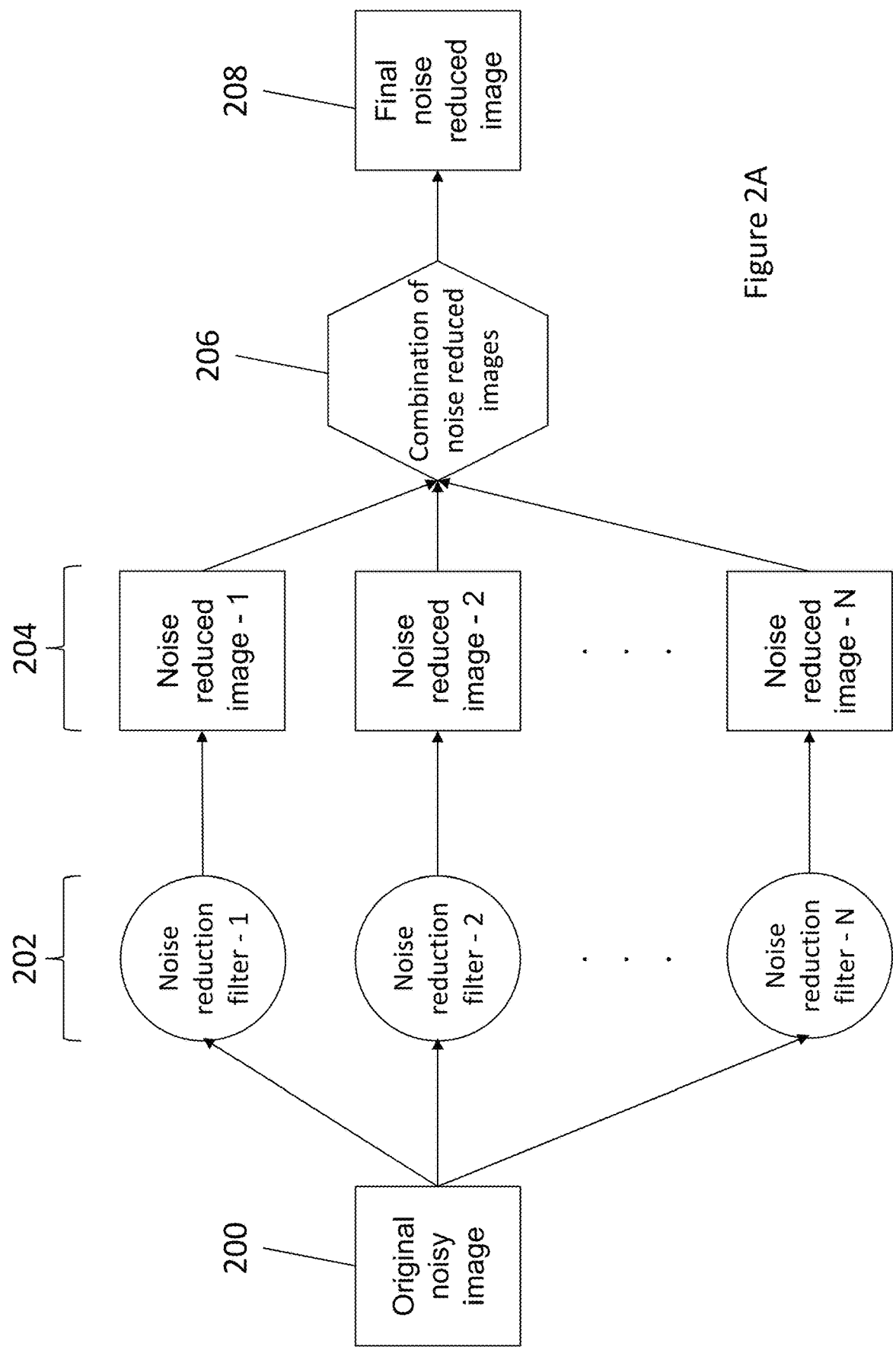
FIGS. 2A and 2B illustrate example noise reduction methods according to the present disclosure.

Because the different types of noise, due to their difference in source, follow different statistical patterns, they should be processed separately. This process is illustrated in the flow chart of FIG. 2A, showing an example noise reduction method according to the present disclosure. As seen therein, a plurality of noise reduction filters 202 (1 to N) are applied to a noisy input image 200. Each noise reduction filter 202 produces a corresponding noise reduced image 204 (1 to N). The filters 202 may be applied in parallel such that each noise reduced image 204 only has the noise reduced that corresponds to the applied filter 202, and thus may still include the other types of noise not reduced by the corresponding filter 202. Of course, actual processing may occur sequentially in time while retaining the parallel nature of the application. The plurality of noise reduced images 204 can then combined 206 to produce a final noise reduced image 208. The combination of noise reduced images results in the final noise reduced image 208 having each type of noise reduced.

Figure 2B:
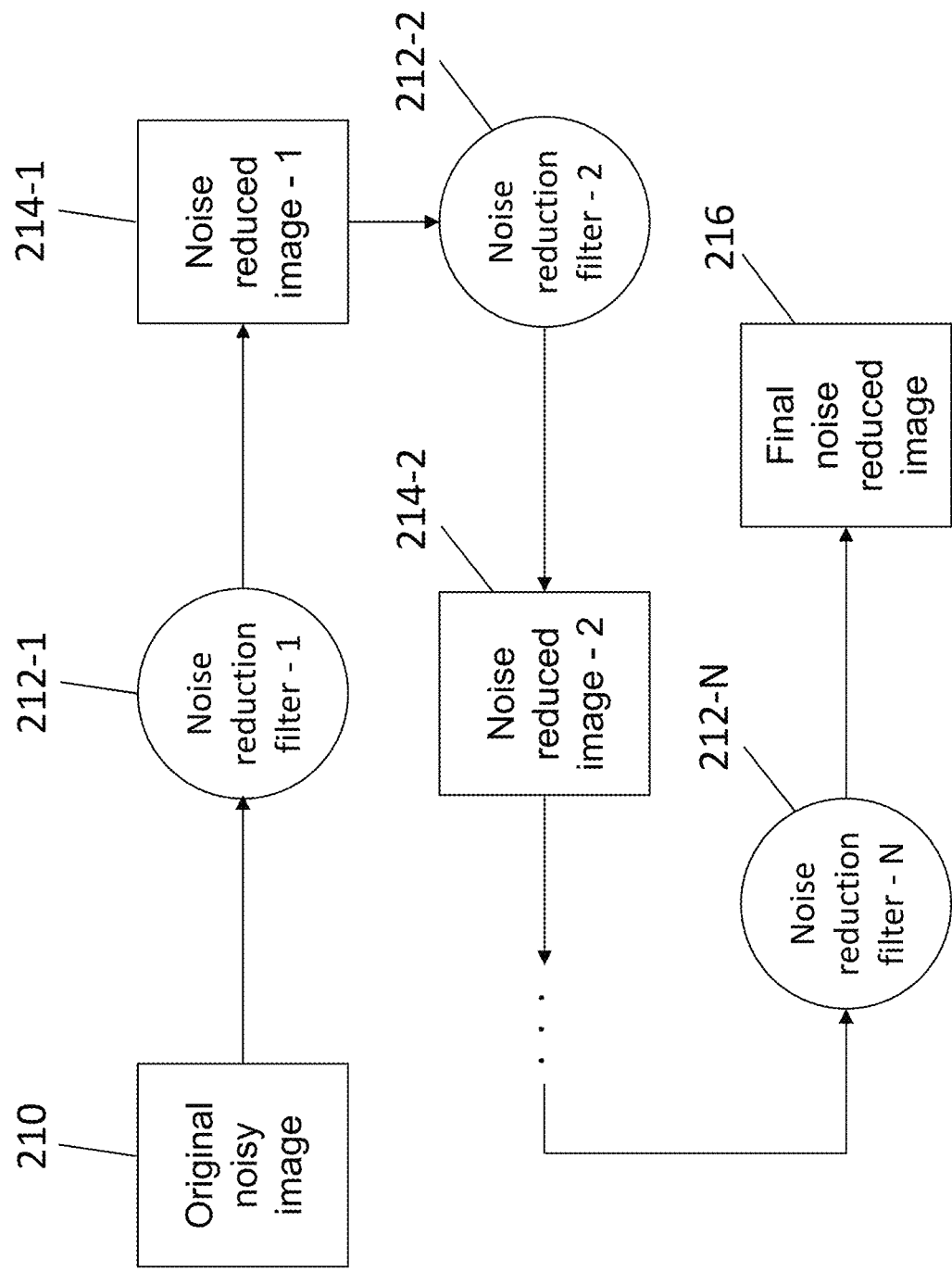

In other embodiments such as those corresponding to FIG. 2B, however, the filters 212-1 to 212-N may be applied sequentially such that a first type of noise is removed by a first filter 212-1 to produce a first noise-reduced image 214-1 in which the first type of noise is removed but other types of noise remain. A second type of filter 212-2 may then be applied to the first noise-reduced image 214-1 to further remove a second type of noise, while still other types of noise remain. This process can be repeated with additional noise reduction filters 212-N until all desired noise is removed and a final noise-reduced image 216 produced.

Figure 3:
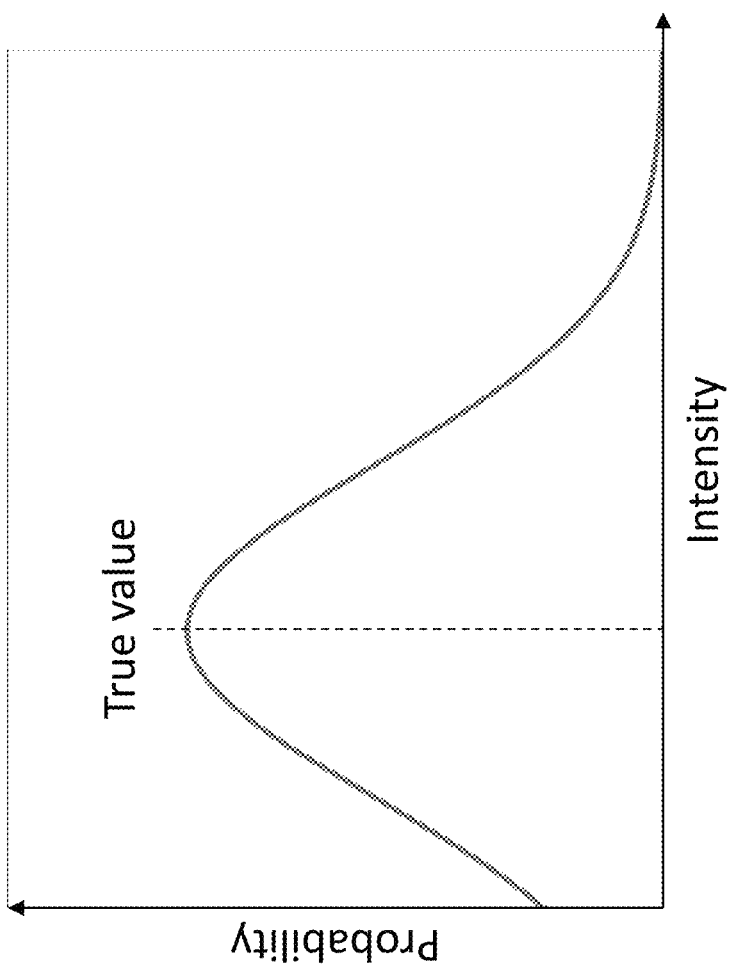
FIG. 3 illustrates an example probability distribution of the intensity of a given pixel.
Figure 4:
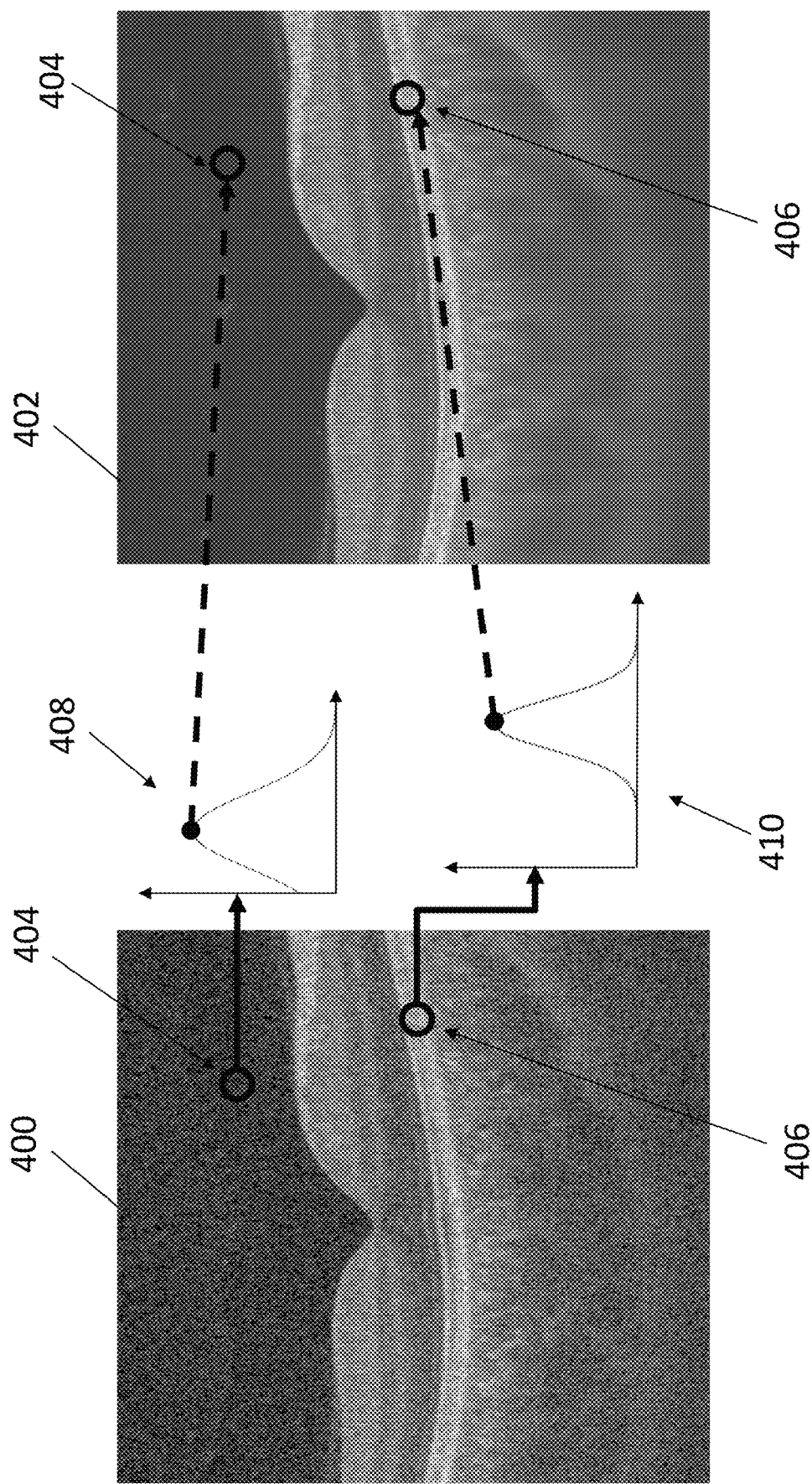
FIG. 4 illustrates different intensity probability distributions for different areas of a B-scan.

Each filter may be designed and applied based on the probability distribution for the relative intensity for the pixels in an image without a given type of noise. For example, the intensity of each pixel in an image, when subject to random noise, can be modeled as shown in FIG. 3. The "true value" (represented by the dashed vertical line) corresponds to the actual intensity of the pixel without any noise. In the probability distribution example of FIG. 3, the 'true value' may be determined as the intensity where probability is a maximum. Each pixel may have its own unique probability distribution. In other words, the noise (type and level) may not be uniform throughout an entire image. For example, as seen in FIG. 4, the intensity probability distribution 408 for a pixel 404 above the retina (having only random system noise) in a B-scan image 400 is skewed toward zero relative to the intensity probability distribution 410 for a pixel 406 in a retinal layer (having random system noise and speckle noise) of the image 400. The 'true value' intensity at the maximum of the probability distribution is shown in a corresponding noise-reduced B-scan image 402 where the intensity of the pixel 404 above the retina is much lower (darker) than that of the retinal pixel 406.

These probability distributions may be different for each type of noise. For example, the intensity probability distribution for pixels without many types of noise may be Gaussian; however, some removal of other noises may cause the intensity probability distributions to follow different statistical models. For noises resulting in the same type of distribution model, removal of each type of noise may result in probability distributions having a different mean, sigma value, or like statistical property.

Therefore, if the intensity probability distribution is understood for the types of noise in each pixel of an image, the noise-free value of each pixel can be reconstructed. For example, the application of each filter may set each pixel of an image to have its true intensity value (e.g., the intensity corresponding to the maximum probability).

Artificial intelligence systems such as deep learning (and other machine learning) models/systems can be used to determine the intensity probability distributions for each pixel (e.g., each location of the retina) to more accurately estimate the most probable intensity value of each pixel. The deep learning systems of each filter are particularly designed and trained to estimate the intensity probability distribution of each pixel. The design and training of the deep learning systems are based on an understanding of the fundamental physics in OCT imaging (or the other coherent imaging methods) so that the systems can be trained with images demonstrating the correct intensity probability distributions.

For example, the deep learning systems can be trained with data sets having two or more images. In each set, the pixel intensity at the same corresponding location among different images is used to construct the intensity probability distribution of that pixel. Put another way, a perfectly large set will include at least one image having every possible intensity for a given pixel location, and the relative number of images in the set having a given intensity represents the corresponding probability of that intensity. Thus, the relative number of images for every intensity value will produce the intensity probability distribution. For sets of fewer images, the same process can be used to generate a probability distribution by fitting the relative number of images of each intensity to a known type of distribution curve. However, as the above description derives probability distribution models based on pixel intensities that retain noise information, the approach alone does not necessarily suppress the different types of noise separately.

To account for the different types of noise, differences between the images of a set can be compared, and adjusted based on the comparison, prior to developing the probability distribution. For example, the effect of random noise can be derived by considering differences between images of a set of B-scan images taken at the same cross-sectional location through the retina. This is because the difference between images of the set will primarily represent random noise, since the underlying structure at the same cross-sectional location generally remains unchanged. Adjusting each image based on these differences has the effect of removing the random noise from the adjusted images. As a result, a probability distribution derived based on the adjusted images is a probability distribution for the image where random noise is suppressed but speckle is largely preserved. In these embodiments, the difference may be determined according to any statistical method, such as by simple subtraction, an average of the differences between each successive scan, or the like; and the adjustments may be made in any statistical manner, such as by subtracting the average difference from each image.

Similarly, the effect of speckle noise can be found from sets of images of B-scans taken from adjacent or nearby locations within a transverse resolution of the imaging system. The differences between the images of such sets will primarily represent speckle noise. Again, the images may be adjusted according to any statistical determination of the difference, so that a resulting intensity probability distribution is one in which the pixel intensity at the maximum probability represents the most probable intensity without speckle noise (e.g., where both speckle noise and random noise are suppressed).

Referring back to FIGS. 2A and 2B, a deep learning system trained to suppress random noise may correspond to noise reduction filter 1 (a sharp filter) 202-1, 212-1 and a deep learning system trained to suppress speckle noise may correspond to noise reduction filter 2 (a smooth filter) 202-2, 212-2. Where deep learning systems are the filters, the original noisy image is input to the trained system (filter), and the output of the trained system is an image in which each pixel is set to the intensity corresponding to the maximum probability. In other words, a trained deep learning system may be one that has been trained to know the intensity probability distribution (or otherwise knows a 'true value' intensity) for each pixel without one type of noise.

Figure 5:
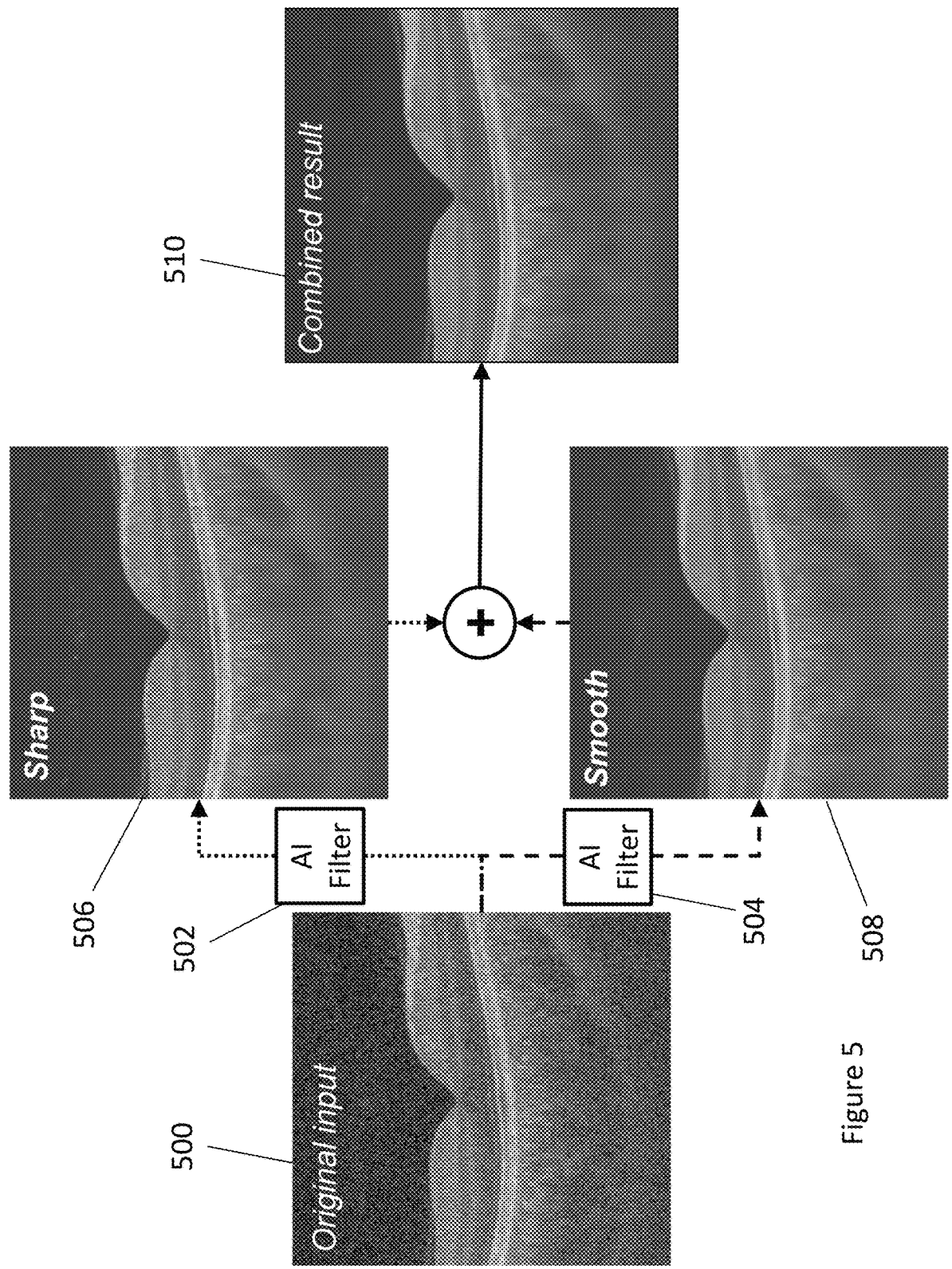
FIG. 5 illustrates parallel filtering of B-scan images to produce a combined noise-reduced image.

Such a configuration where separately trained deep learning systems filter an original input B-scan image to produce a combined noise-reduced image is illustrated in FIG. 5. More particularly, an original input image (e.g., an OCT B-scan) 500 is input to both a trained machine learning system 502 providing a sharp filter and a trained machine learning system 504 providing a smooth filter. The sharp filter 502 produces an image 506 with reduced random noise and the smooth filter produces an image 508 with reduced speckle noise. These reduced noise images 506, 508 are then combined to produce a final noise-reduced image 510 with both random and speckle noises reduced.

In still other embodiments, any type of filter capable of reducing a desired type of noise may be used. Such filters may include median filters, Gaussian filters, spectral domain filters, and the like.

The noise-reduced images output by each filter can be combined according to any statistical combination method. For example, each noise-reduced image can be combined through a weighted average technique where the weight of each image is adjusted to match the relative noise level of the corresponding noise type. In other words, each noise-reduced image can be weighted according to the amount of the corresponding noise in the original input image. Considering the example of FIG. 5, the output weights are 0.2 for the sharp filter (meaning 20% of the noise is random) 502 and 0.8 for the smooth filter (meaning 80% of the noise is speckle noise) 508.

Figure 6:
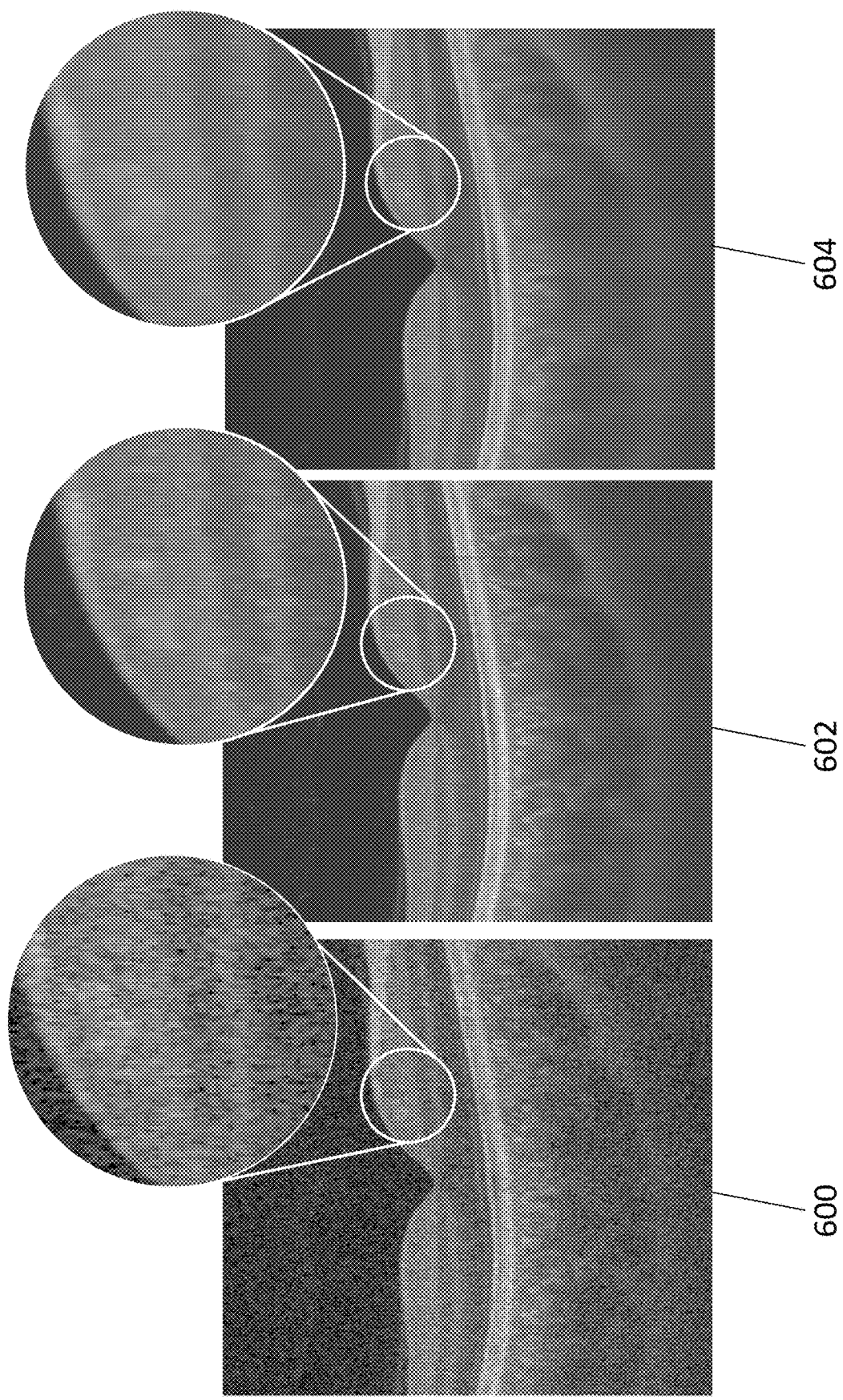
FIG. 6 illustrates a comparison of a noise reduction method according to the present disclosure and a noise reduction method based on averaging.

By way of comparison, combining the outputs of each filter can produce a final noise-reduced image comparable to an image produced by averaging 128 images taken at the same location (a traditional technique for suppressing noise). FIG. 6 shows such a comparison, where an original input image (without any noise reduction) 600, an image produced by averaging 128 images from substantially the same location (including the original input image) 602, and an a noise reduced image 604 resulting from the above-described combination of outputs of a smooth filter and a sharp filter. As can be seen in the entire B-scan, and in the enlarged portions, separately applying different types noise reduction and then combining the outputs of the filters produces comparable or better results to the averaging, both clearly having less noise than the input image. However, with the method described herein, only one B-scan image is needed to be filtered, rather than the many needed if reducing noise by averaging or the perpetuated errors introduced if reducing noise based on a system trained by averaging.

Figure 7:
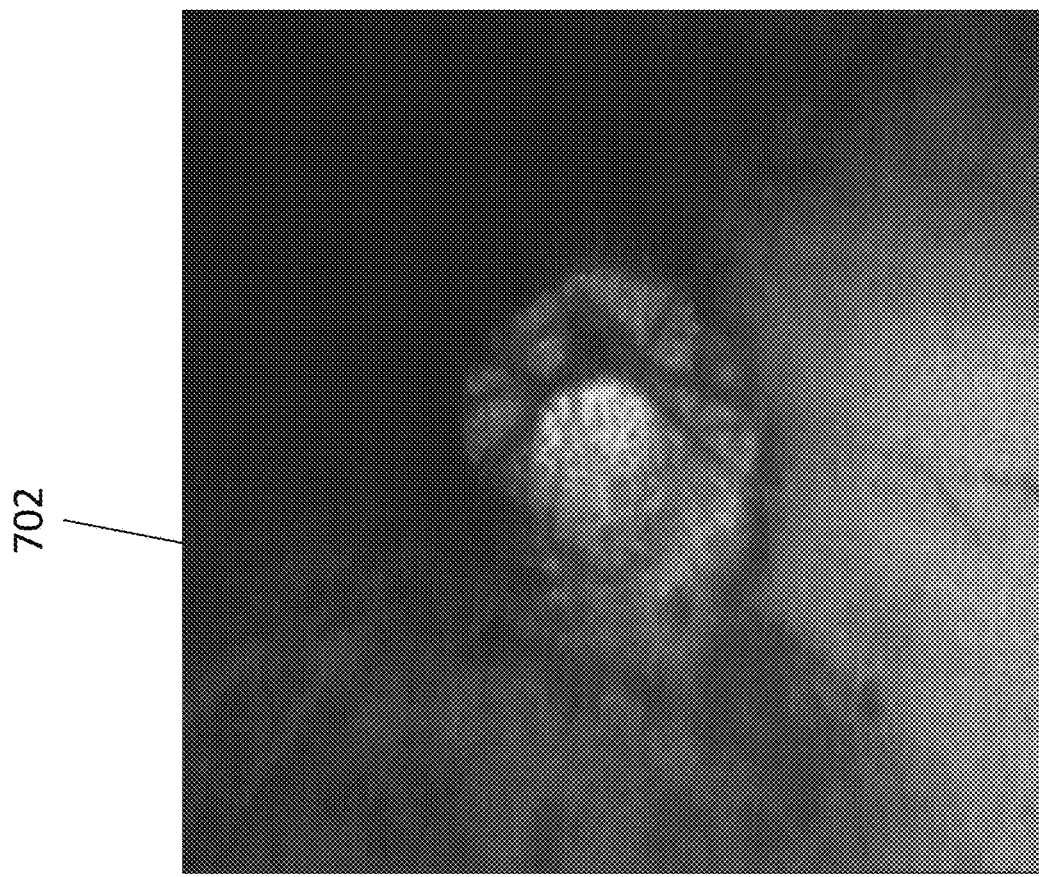
FIG. 7 illustrates original and noise-reduced 1-pixel depth en-face images of the lamina cribrosa.
Figure 7:
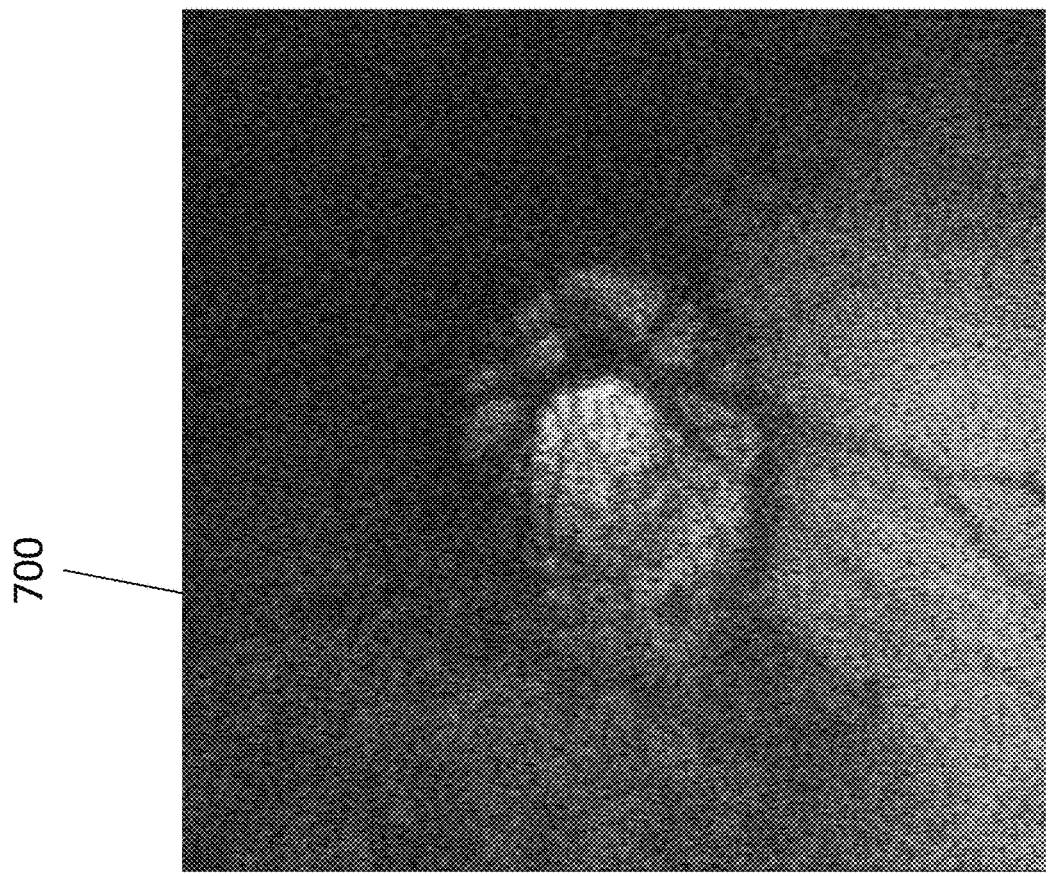

Other embodiments may use additional filters, or use the filters individually. For example, the noise-reduced output image 508 of the smooth filter 504 (removing speckle noise) has smoother retinal boundaries than image 506 output by the sharp filter 502. Therefore, the smoothed image 508 (rather than the output from the sharp filter, or the combined output image) may be best used in tasks such as visualization/display and layer segmentation. FIG. 7 illustrates this concept with respect to 1-pixel depth en-face images of the lamina cribrosa, where the primary noise component is speckle noise. As seen in FIG. 7, the noise-reduced image 702 filtered only with a smooth filter to reduce speckle noise is smoother and more visually appealing than the original image 704. Thus, the speckle noise-reduced image 704 output from the smooth filter may be beneficial for improving visualization applications.

Figure 8:
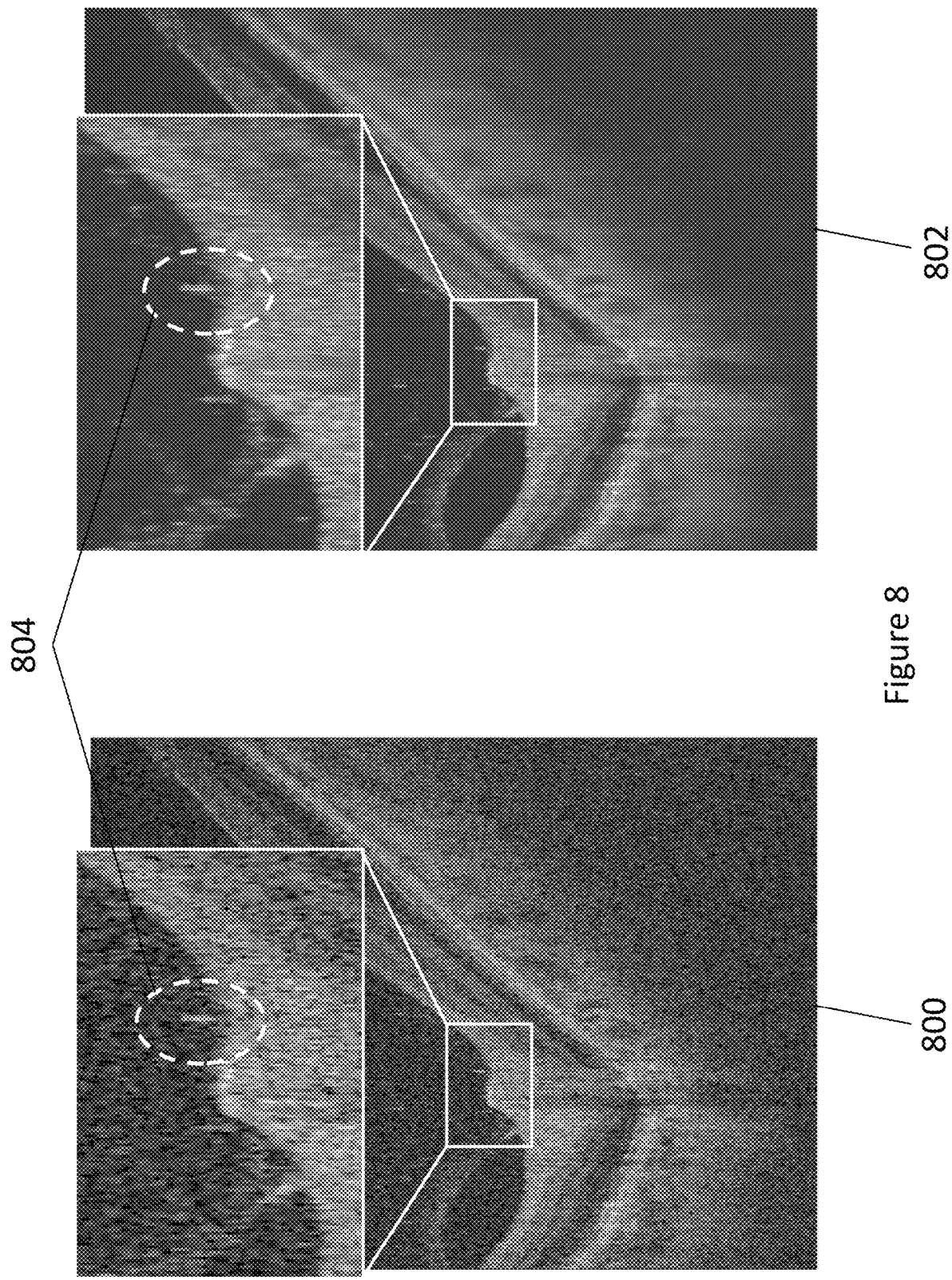
FIG. 8 illustrates original and noise-reduced B-scan images showing an inflammatory cell.

Similarly, because the noise reduced output image 506 of the sharp filter 502 preserves speckle information, it may be best used in tasks such as abnormality detection (identifying inflammatory cells) or OCT angiography (which relies on differences between images at a common location to indicate blood flow). For example, FIG. 8 illustrates an original B-scan image 800 and a noise-reduced B-scan image 800 output by a sharp filter to remove random noise. In both images 800, 802, an inflammatory cell(s) (circled) 804 is visible. However, the cell 804 is more identifiable in the random noise-reduced image 802 as it is against a clearer background.

During the training of the deep learning systems for noise-reduction filtering, additional information such as the retinal layers, are implicitly learned. This results from the different statistical properties of noise associated with pixels of each retinal layer. As the deep learning system is trained to reduce the different noises (types and levels) in different retinal layers, it thus also learns which pixels are associated with each layer. Put another way, for the deep learning systems to remove proper noise types and levels from each retinal layer, it should know to which layer each pixel belongs. With such knowledge, layer boundaries can be identified, and segmentation realized, by determining the pixels at which the associated layers change.

Figure 9:
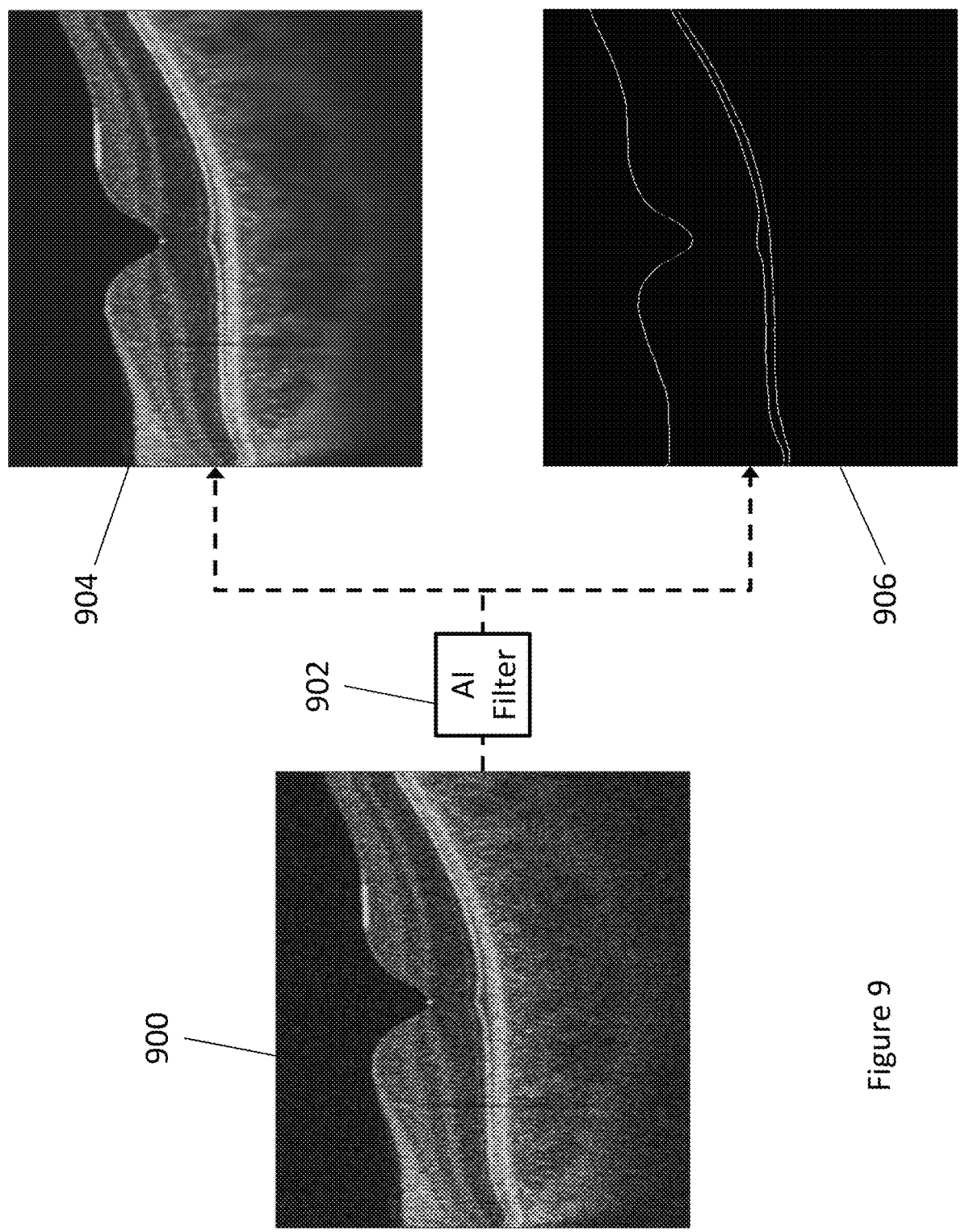
FIG. 9 illustrates an output of trained deep learning system including a noise-reduced image and a segmentation of the image.

Thus, in some embodiments, noise-reduction filters and segmentation detectors can be trained simultaneously as part of the same deep learning system. Such an output is illustrated in FIG. 9, where an original image 900 is input into a trained deep learning system 902, which outputs a noise-reduced image 904 and a retinal segmentation 906 of the image. The segmentation 906 includes (from top to bottom) boundaries of the inner limiting membrane (ILM), retinal pigment epithelium (RPE), and Bruch's membrane layers.

While 2D images such as B-scans have generally been described, the above method and corresponding system could be applied to any type of image. For example, the input may be a single optical coherence tomography (OCT) (or like coherent imaging modality) B-scan, a 3D volumetric scan, an en face image or C-scan, an angiographic B-scan image, an angiography en face image or C-scan, or like images from other imaging modalities.

Figure 10:
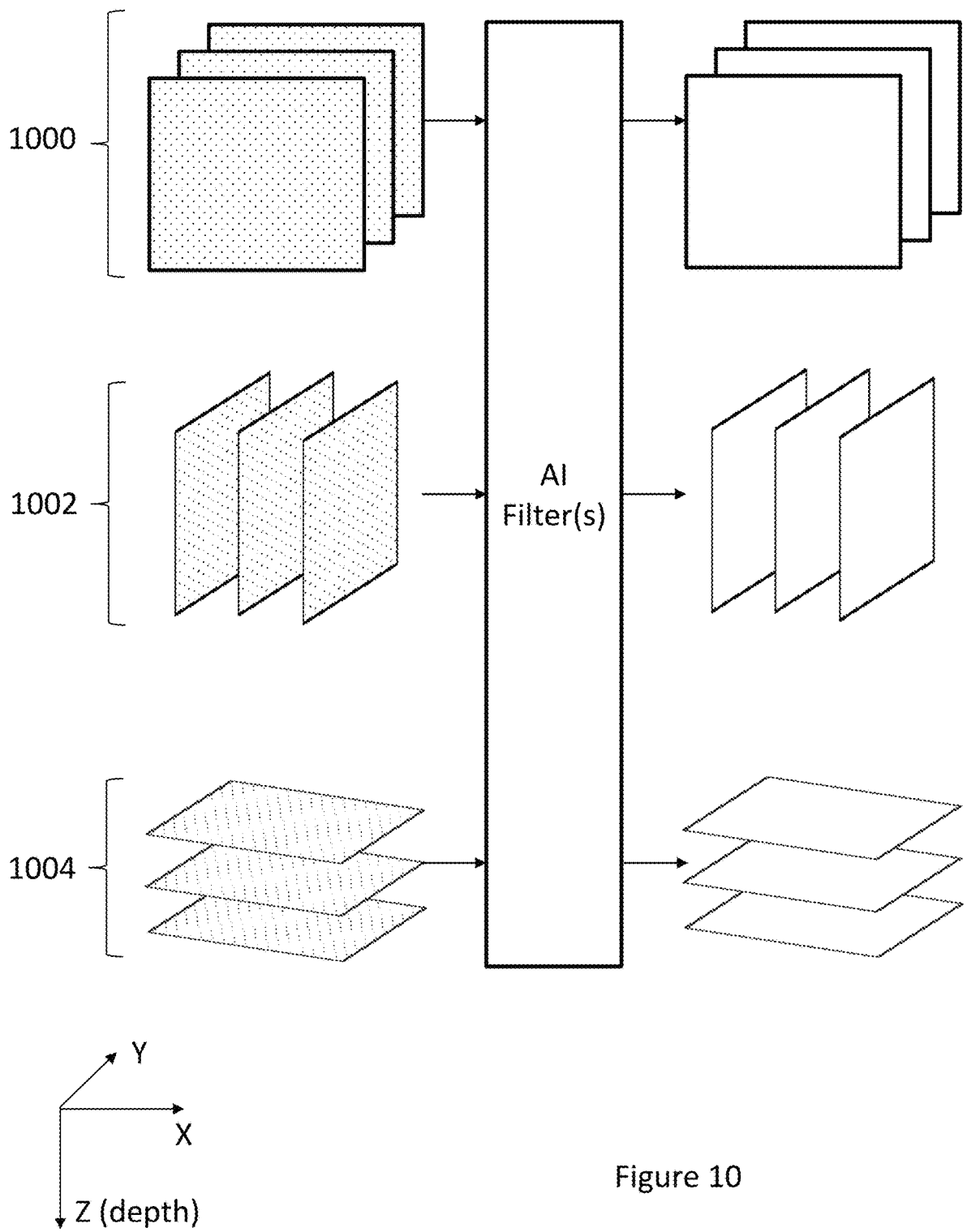
FIG. 10 illustrates 3D noise reduction according to the present disclosure with different planes.

When using the methods described herein to reduce noise for 3D volumetric data (e.g., 3D OCT structural data, 3D OCT-angiography data), the noise reduction can be performed in different planes of 2D images that collectively form the 3D volumes, as shown in FIG. 10. In these embodiments, the noise (types and levels) may be different depending on the location in the volume (either at different depths, or different locations). Accordingly, different noise reduction filters may be applied to different portions of the volume. These filters, if trained machine learning systems, may be trained for different types of noise and/or the different effects of noise at different locations in the volume. Weights used to combine differently filtered images, or other combination techniques, may also be variable and change depending on where in the volume the images are located.

Any of the volumetric data may be noise reduced according to the above-described methods. For example, collections of B-scans in the X-Z plane 1000 as described above can be individually noise reduced to reduce noise of an entire volume. In other embodiments, the data may be sampled (or re-sampled) in the Y-Z plane and noise reduction as described above applied on Y-Z B-scans 1002. Similarly, the noise reduction process can be applied on X-Y plane C-scans or en face images flattened over any depth/thickness and/or with respect to any reference layer. Such a reference layer may be the separation between two retinal tissue layers, for example, the ILM.

Figure 11A:
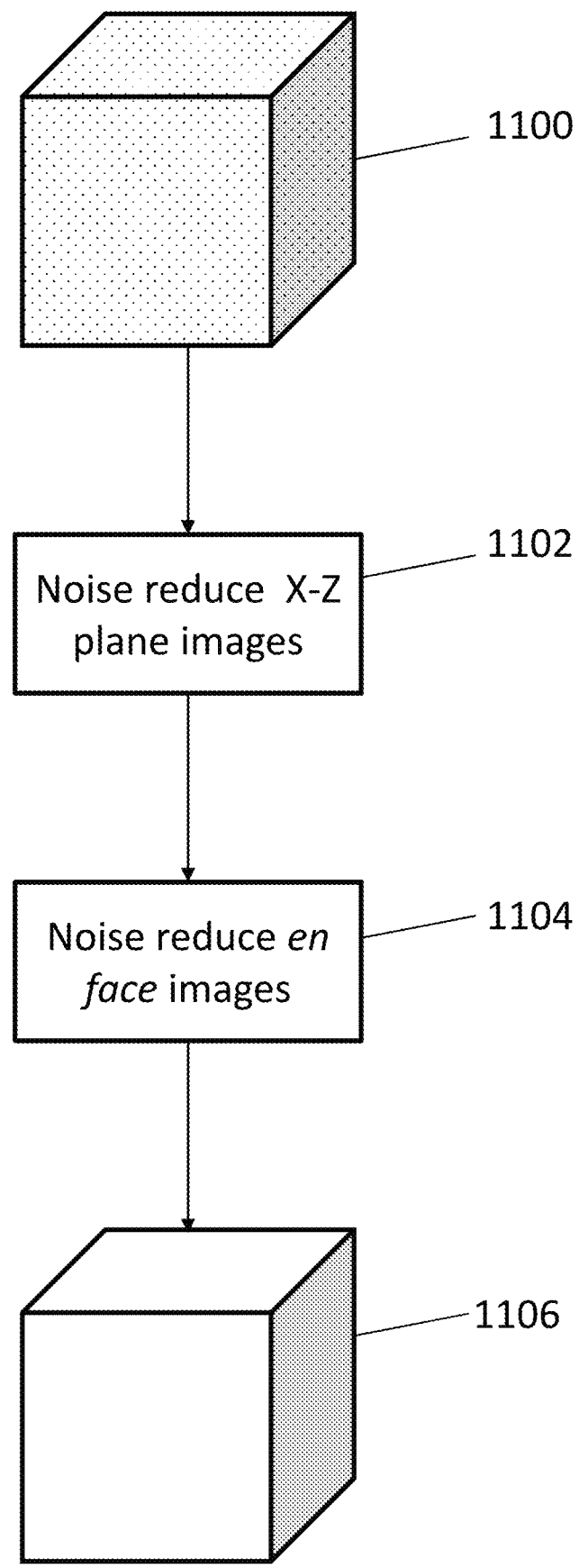
Figure 12:
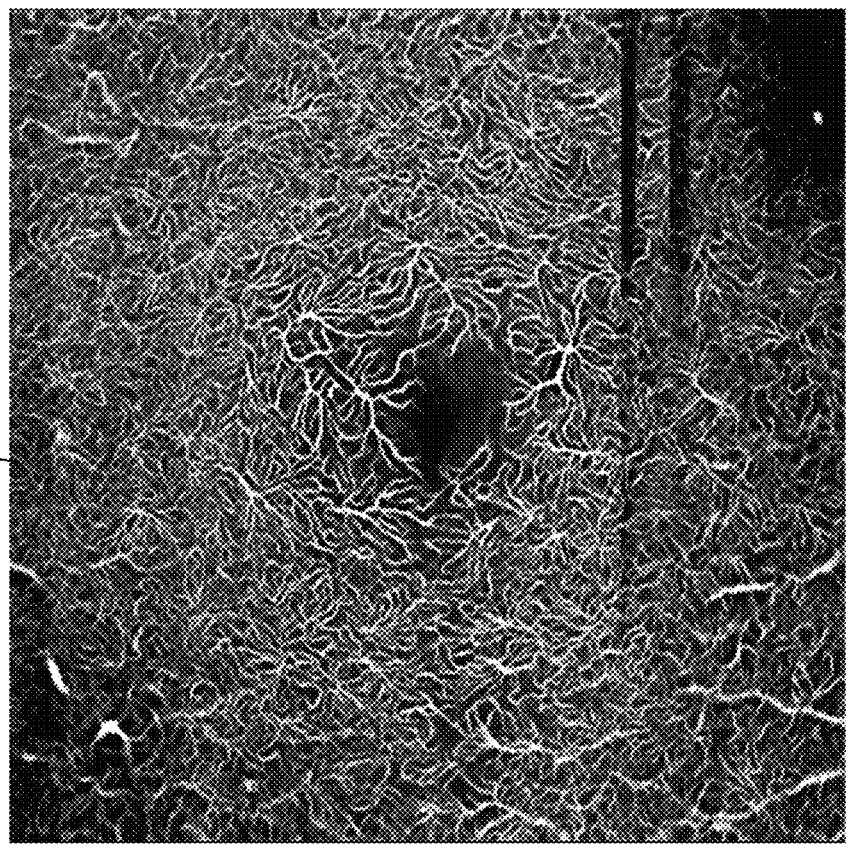
FIG. 12 illustrates an example of noise reduction according to the method of FIG. 11A.
Figure 12:
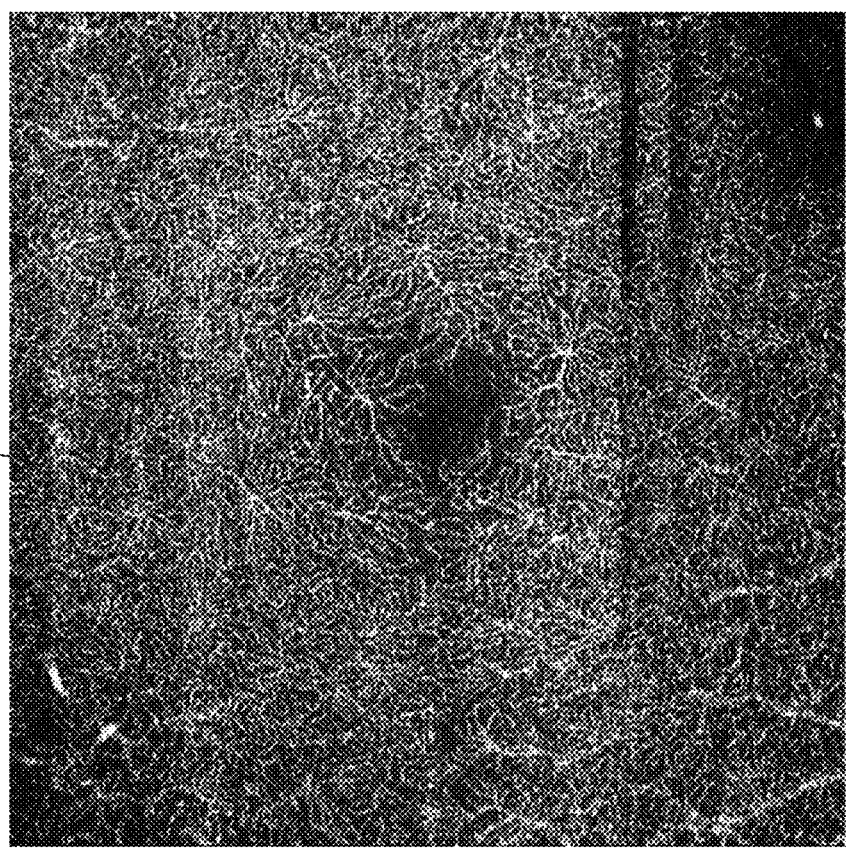

In some embodiments, filtering can be applied to different planes of 2D images of a 3D volume or other collection of 2D images (e.g., from non-adjacent locations of a larger 3D volume). Just as with the application of individual filters to the 2D images, the application of filters to different planes can be in parallel and combined, or sequential. FIG. 11A illustrates a first example of sequential noise reduction of a 3D volume (e.g., an OCT-angiography (OCT-A) volume). According to the example of FIG. 11A, a first step of noise reducing a 3D OCT-A volume 1100 involves noise reduction of OCT-angiography images in X-Z plane 1102 of the volume 1100, and a second step involves noise reduction of en face images 1104 of the volume 1100, to produce a final noise-reduced 3D volume 1106. FIG. 12 illustrates a comparison of an en face image 1200 of the deep plexiform layer taken from the original OCT-A volume 1100, and of a en face image 1202 of deep plexiform layer noise-reduced by the method of FIG. 11A. As can be seen in FIG. 12, vessel connectivity is greatly enhanced after noise reduction.

FIGS. 11B and 11C illustrate similar sequential methods with other combinations of planes. In the example of FIG. 11B, X-Z plane images 1112 from an original 3D volume 1110 are first filtered, followed by Y-Z plane images 1114 and then X-Y plane images 1116, to produce a final noise-reduced volume 1118. And in the example of FIG. 11C, X-Y plane images 1122 from an original 3D volume 1120 are first filtered, and then X-Z plane images 1124 are filtered to produce a final noise-reduced volume 1126. As above, the different filterings may be directed to a type of noise and/or the plane in which it is applied.

Each filtering step may be performed by a filter trained or otherwise designed to remove a different type of noise and/or to identify noise in the respective plane in which it is applied. Removing a different type of noise in each filter step may be beneficial where each type of noise in more apparent in a different plane, whereas removing the same type of noise in multiple steps may be beneficial where one type of noise expresses itself differently in different planes. Where different types of noise are removed, the images of the plane in a subsequent filtering step may be generated from the original volume after a preceding noise reduction step. Accordingly, the subsequently generated images may already have the preceding type of noise removed. By sequentially applying the filters, a volume reconstructed from the finally filtered images represents a noise-reduced volume.

Figure 11D:
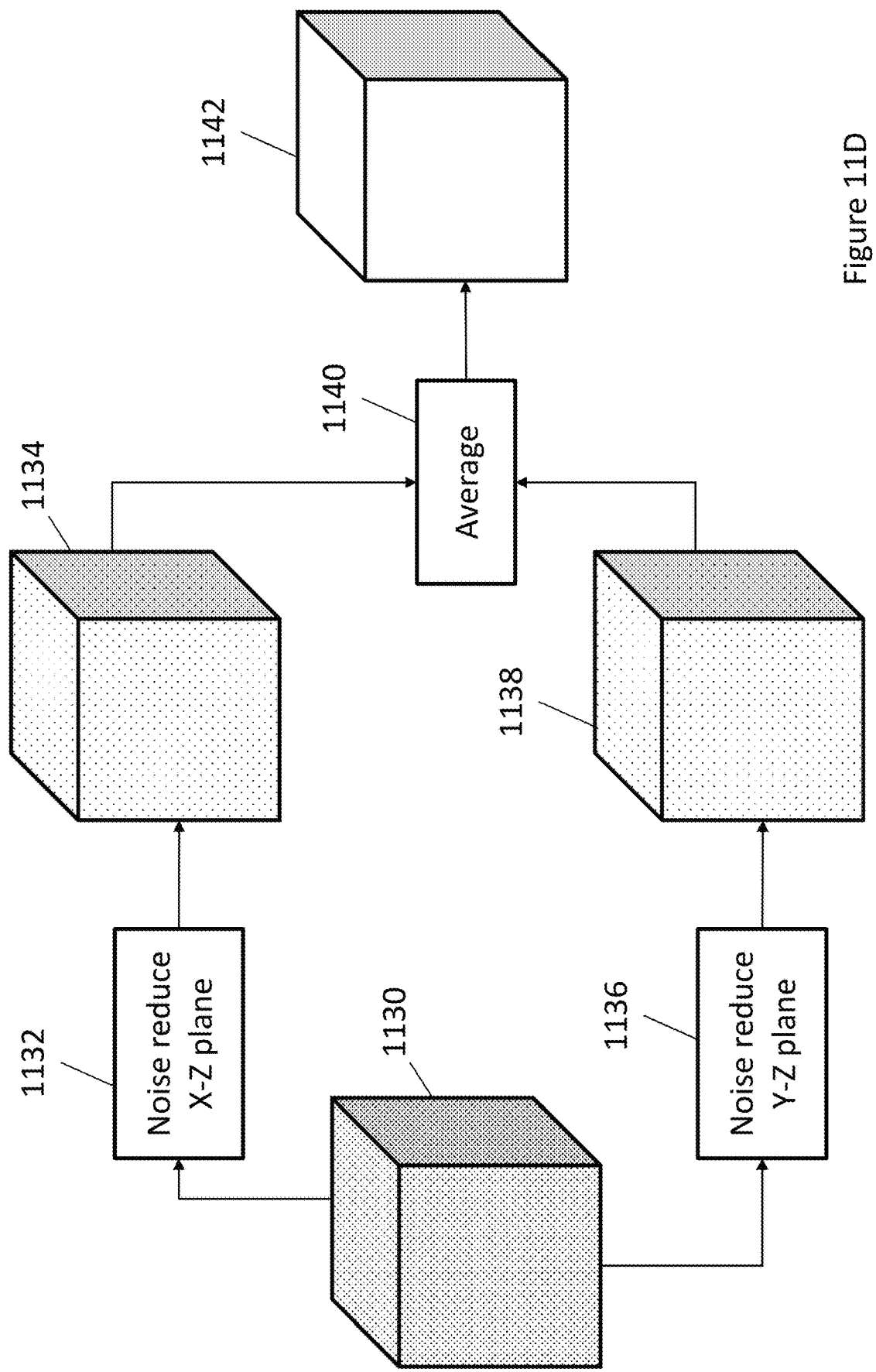

While each of FIGS. 11A-11C represent the sequential application of filters where subsequent filters are applied to images in which some noise has already been reduced, other embodiments may apply filters in parallel. An example of noise reduction for different planes in parallel is shown in FIG. 11D. Therein, noise reduction is separately performed in parallel on images of the X-Z plane 1132 and the Y-Z plane 1136 of an original 3D volume. As above, performing noise reduction in parallel refers to performing the noise-reduction on images of a 3D volume not subject to the other noise-reduction application. Accordingly, the actual application of the noise-reduction may still be performed sequentially in time. The resulting noise-reduced volumes 1134, 1138 may be averaged (e.g., by weighted averaging or other combination techniques as described above) to produce a final noise-reduced volume 1142. Of course, different planes and combinations may be used in parallel in other embodiments.

The present disclosure provides various improvements compared to traditional noise reduction techniques (such as averaging 128 images taken from a single location). For example, it can take a relatively long time to obtain 128 images (or any number of images being averaged), which limits the total imaging speed and makes the variously averaged images more susceptible to motion artifact. Additionally, it is practically difficult to take so many images at a single location; therefore, each image of the average may include different information. Put another way, an imaging target at that location may not present in every image, or other elements may be confused as the imaging target. Further, to the extent any other machine learning systems are trained with the above-described average images as supervisory training data, the inherent limitations of averaging are imputed into the trained machine learning system.

In addition, it has been empirically observed that the presently described noise reduction preserves the quantitative information available in the original images. Thus, the present noise reduction technique enables applications which were previously only achievable with high-speed devices (e.g. variable interscan time analysis (VISTA) systems), where the high-speed is used to take multiple repeated scans to suppress noise, possible on low-speed devices with fewer repeats. In particular such applications include angiographic imaging (e.g., OCT-A) and the like where imaging is of, or based on, dynamic (non-static) structures (e.g., movement of cells, such as red blood cells). Further in this vein, the noise reduction described herein may be used in at or near real-time imaging applications. In some embodiments, the input images may be obtained with high speed OCT imaging (e.g., operating at a 400 kHz A-line scanning rate), such that the filtering according to the present disclosure provides high fidelity images at that high speed. As a result, noise-reduced 3D volumes, cross-sectional images (B-scan or C-scan images), or en face images can be displayed concurrent (or nearly concurrently) with their imaging.

A system for executing the above-described methods is also contemplated within the scope of the present disclosure. Such a system may include a computer having one or more processors (e.g., in the form of an integrated circuit(s), discrete circuitry, or the like) for executing the method, storage (such as a hard disk, memory, RAM, or the like) and an input/output interface (e.g., display, keyboard, mouse, and the like). The above-described filters may be implemented via software executed by the processor(s) or hardware (e.g., via circuitry, optical filters, or the like) depending on the desired filtering. The storage may be located locally with the computer, or remotely, for example at a centralized database, and store the software instructions for executing the method and filtering, the filtered images and/or volumes, and/or the resulting noise-reduced images and/or volumes. The system may also be integrated or separate from a system used to obtain the images of the object to be processed. For example, the computer may be the same as that used to control an OCT system.

It is again noted that while OCT ophthalmological imaging is used as an example modality and application thereof herein, the present disclosure is applicable to all types of coherent imaging modalities for any application producing multiple types of noise (e.g., random and speckle noise). Additionally, although two filters are described herein, additional filters may be used and any combination thereof may be used as a final output image. Still further, in some embodiments it may be desirable to apply two or more filters in series, the series filters still being a parallel filtering path to other filters. In some embodiments, the filtering may be applied to any combination of 2D images (from any combination of planes), 3D volumes, and/or collections of 2D images from different locations in a 3D volume.

What is claimed is:

1. An image processing method comprising:
applying a first filter to an input image, thereby generating a first noise-reduced image;
applying a second filter to the input image, thereby generating a second noise-reduced image; and
combining the first noise-reduced image and the second noise-reduced image, thereby generating a final noise-reduced image,
wherein the first filter is configured to suppress a first type of noise from the input image and the second filter is configured to suppress a second type of noise from the input image, the first and second types of noise being different,
wherein the first filter is a first machine learning system trained with images taken from the same or substantially the same location as the input image,
wherein the second filter is a second machine learning system trained with images taken from locations that are adjacent to or nearby a location of the input image, and
wherein training images for the first and second filters each comprise at least one image taken from a different subject than the input image.

2. The method of claim 1, wherein the first noise-reduced image and the second noise-reduced images are combined by weighted averaging, the first noise-reduced image being weighted according to a level of the first type of noise in the input image and the second noise-reduced image being weighted according to a level of the second type of noise in the input image.

3. The method of claim 1, wherein the first noise-reduced image and the second noise-reduced images are combined by a machine learning system.

4. The method of claim 1, wherein an intensity of at least one pixel of the first noise-reduced image is set by the first filter to correspond to a maximum intensity of a probability distribution of intensities of pixels at a corresponding location of an object in the image.

5. The method of claim 4, wherein the probability distribution is determined by a machine learning system.

6. The method of claim 1, wherein the first type of noise is random noise or noise caused by an imaging system that captured the input image.

7. The method of claim 1, wherein the second type of noise is speckle noise.

8. The method of claim 1, wherein the input image is an optical coherence tomography (OCT) or OCT-angiography B-scan image.

9. The method of claim 1, wherein the input image is an en face optical coherence tomography (OCT) or OCT-angiography image.

10. The method of claim 1, wherein the input image is obtained by an optical coherence tomography imaging system configured to operate at least at a 400 kHz A-line rate.

11. The method of claim 1, wherein the input image is an image of a retina.

12. The method of claim 1, further comprising:
segmenting the input image as a result of applying the first filter and the second filter.

13. The method of claim 1, further comprising:
displaying the final noise-reduced image in real-time with the capturing of the input image.

* * * * *